(12) United States Patent
Carignan et al.

(10) Patent No.: US 6,319,257 B1
(45) Date of Patent: Nov. 20, 2001

(54) INSERTER ASSEMBLY

(75) Inventors: Roger G. Carignan; Robert A. Bruce, both of Ventura, CA (US)

(73) Assignee: Kinamed, Inc., Camarillo, CA (US)

( * ) Notice: Subject to any disclaimer, the term of this patent is extended or adjusted under 35 U.S.C. 154(b) by 0 days.

(21) Appl. No.: 09/468,625

(22) Filed: Dec. 20, 1999

(51) Int. Cl.$^7$ .................................................... A61B 17/88
(52) U.S. Cl. ............................................. 606/99; 606/205
(58) Field of Search .............................. 606/99, 61, 205, 606/206, 207

(56) References Cited

U.S. PATENT DOCUMENTS

| | | | |
|---|---|---|---|
| D. 331,625 | 12/1992 | Price et al. ......................... | D24/133 |
| 2,549,731 | * 4/1951 | Wattley ............................... | 439/482 |
| 3,136,040 | * 6/1964 | Bauer et al. ......................... | 29/739 |
| 3,844,291 | 10/1974 | Moen .................................. | 128/354 |
| 3,848,601 | 11/1974 | Ma et al. ............................. | 128/305 |
| 4,349,921 | 9/1982 | Kuntz ................................. | 3/1 |
| 4,501,269 | 2/1985 | Bagby ............................. | 128/92 G |
| 4,545,374 | 10/1985 | Jacobson ........................ | 128/303 R |
| 4,592,347 | 6/1986 | Mahruki ............................ | 128/127 |
| 4,714,469 | 12/1987 | Kenna ................................. | 623/17 |

(List continued on next page.)

FOREIGN PATENT DOCUMENTS

| | | |
|---|---|---|
| 3023942A1 | 1/1982 | (DE) . |
| 0333990 A2 | 1/1989 | (EP) . |
| 0333990 A3 | 1/1989 | (EP) . |

OTHER PUBLICATIONS

Danek, Sofamor; Current Concepts in Spinal Endoscopy; Course Schedule, 1995.
Danek, Sofamor; Laparoscopic Bone Dowell Instruments; Brochure, 1995.
Danek, Sofamor; Laparoscopic Bone Dowel Surgical Technique; Brochure; 1995.

*Primary Examiner*—Gene Mancene
*Assistant Examiner*—Michael B. Priddy
(74) *Attorney, Agent, or Firm*—Christopher Darrow; Oppenheimer, Wolff & Donnelly (57) ABSTRACT

The present invention is directed to an apparatus and method of quickly and easily grasping and releasing a graft. The apparatus includes a sleeve with an opening through the axis of the sleeve. Within the opening of the sleeve is a shaft with a jaw on one end, and a threaded end on the opposite end. The sleeve has a square tip end that is adjacent to the jaw of the shaft. Furthermore, the shaft near the jaw has a square cross-section so that the shaft is substantially prevented from rotating but allowed to move axially along the opening of the sleeve. A knob is also rotatably coupled to the opening of the sleeve on the opposite end of the tip end. The knob has a protruding end which has an outer thread on the surface of the protruding end and a center thread. The outer thread of the protruding end is adapted to rotatably couple to the opening on the sleeve, and the center thread of the protruding end is adapted to rotatably couple to the threaded end of the shaft. The opening on the sleeve and the outer thread on the protruding end of the knob are threaded such that clockwise rotation of the knob extends the knob relative to the opening on the sleeve. Furthermore, the threaded end of the shaft and the center thread of the protruding end are threaded such that clockwise rotation of the knob retracts the shaft into the center thread of the protruding end. The net result is that as the knob is turned clockwise, the shaft is pulled into the opening of the sleeve at a faster rate because the knob is extending away from the sleeve and the shaft is being inserted into the protruding end of the knob at the same time. As the shaft is being retracted into the tip end of the sleeve, the tip end bears on the jaw to close the jaw quickly and conversely opens quickly as the shaft protracts from the tip end.

24 Claims, 5 Drawing Sheets

U.S. PATENT DOCUMENTS

| | | | |
|---|---|---|---|
| 4,743,256 | 5/1988 | Brantigan | 623/17 |
| 4,753,235 | 6/1988 | Hasson | 128/321 |
| 4,834,757 | 5/1989 | Brantigan | 623/17 |
| 4,877,020 | 10/1989 | Vich | 128/92 V |
| 4,878,915 | 11/1989 | Brantigan | 623/17 |
| 4,936,848 | 6/1990 | Bagby | 623/17 |
| 4,961,740 | 10/1990 | Ray et al. | 606/61 |
| 4,997,432 | 3/1991 | Keller | 606/61 |
| 5,015,247 | 5/1991 | Michelson | 606/61 |
| 5,055,104 | 10/1991 | Ray | 606/61 |
| 5,192,327 | 3/1993 | Brantigan | 623/17 |
| 5,258,005 * | 11/1993 | Christian | 606/205 |
| 5,258,007 * | 11/1993 | Spetzler et al. | 606/208 |
| 5,397,364 | 3/1995 | Kozak et al. | 623/17 |
| 5,423,855 | 6/1995 | Marienne | 606/208 |
| 5,425,772 | 6/1995 | Brantigan | 623/17 |
| 5,431,675 * | 7/1995 | Nicholas et al. | 606/170 |
| 5,439,464 | 8/1995 | Shapiro | 606/83 |
| 5,443,514 | 8/1995 | Steffee | 623/17 |
| 5,472,439 * | 12/1995 | Hurd | 606/1 |
| 5,474,566 * | 12/1995 | Alesi et al. | 606/139 |
| 5,484,437 | 1/1996 | Michelson | 606/61 |
| 5,499,997 | 3/1996 | Sharpe et al. | 606/206 |
| 5,514,148 | 5/1996 | Smith, III | 606/151 |
| 5,782,747 * | 7/1998 | Zimmon | 600/104 |
| 5,782,830 | 7/1998 | Farris | 606/61 |
| 5,993,474 * | 11/1999 | Ouchi | 606/206 |
| 6,066,174 * | 5/2000 | Farris | 623/17 |

\* cited by examiner

INSERTER ASSEMBLY

BACKGROUND OF THE INVENTION

1. Field of the Invention

This invention relates generally to an inserter device assembly and, more particularly, to an inserter assembly and a method for quickly grasping and releasing a variety of sizes of surgical implants.

2. Description of the Related Art

When invertebral (spinal) discs become herniated or rupture, they are surgically removed and replaced with bone grafts to fill the invertebral space to prevent the disc space from collapsing and to promote fusion of the adjacent vertebrae across the space. For example, in the Smith-Robinson technique for cervical fusion, the surgeon prepares the end plates of the adjacent vertebral bodies to accept a graft after the disc has been removed. The end plates are generally prepared to have parallel surfaces using a high speed burr. The surgeon sculpts the graft to fit tightly between the bone surfaces so that the graft is held by compression between the invertebral bodies. The bone graft is intended to provide structural support and promote ingrowth to achieve a solid fusion of the adjacent vertebra.

To insert the graft, surgeons have used a number of surgical instruments to grasp the graft and to position the graft between the prepared parallel surfaces. Unfortunately, the surgical instruments currently used to insert the graft have exhibited a number of shortcomings. For example, U.S. Pat. No. 5,782,830 issued to Farris discloses an actuator that slides over a jaw to close and open the jaw. One of the disadvantages here is that the pressure applied to the jaw is imprecise and the surgeon has to use both hands to hold the handle and the actuator to implant the graft. Further, the actuator is located close to the distal end of the instrument such that manipulation of the actuator may need to occur in the surgical wound were space is limited. Also, because of the large diameter of the actuator, it impedes the view of the surgical area. Another example is U.S. Pat. No. 5,443,514 issued to Steffee, which discloses an instrument 80 in FIGS. 4 through 7. Here, rotating the handle causes the jaw to open and close. However, it takes a number of turns to fully open and close the jaw which wastes valuable time when time is of the essence in surgery such as this. Also, when the handle is rotated to open the jaws the jaws are not forcibly actuated into the open position by this rotation.

Therefore, there is still a need for an insertion device that can quickly grasp and release a graft with precise pressure, allow actuation of the jaws to occur at the proximal end of the instrument and at the same time does not inhibit viewing of the surgical area.

OBJECT AND SUMMARY OF THE INVENTION

A general object of the present invention is to provide an inserter device assembly that can quickly grasp and release a surgical implant.

A general object of the present invention is provide an inserter device assembly that can quickly grasp and release a surgical implant.

Another object of the present invention is to provide an inserter device assembly that can grasp a variety of sizes of surgical implants.

Yet another object of the present invention is to provide an inserter device assembly that can be easily and quickly assembled and disassembled so that it saves time during the surgery to assemble the inserter device and later saves time disassembling the inserter device so that it can be cleaned and sterilized thoroughly.

Still another object of the present invention is to provide an inserter device assembly that does not obstruct the surgeon's view of the surgical area.

In general, these and other objectives are accomplished by providing the instrument with a sleeve, a shaft, and a knob. The sleeve has an opening running through the center axis. On one end of the shaft, the shaft splits into a fork to form an arc jaw, while the opposite end of the shaft is threaded. The knob has a protruding end which has an outer thread on the surface of the protruding end and an inner thread aligning with the center axis. The outer thread of the protruding end is adapted to rotatably couple to the opening on one end of the sleeve, and the inner thread of the protruding end is adapted to rotatably couple to the threaded end of the shaft. The opening on the sleeve and the protruding end are threaded such that clockwise rotation of the knob extends the knob relative to the opening on the sleeve. Furthermore, the threaded end of the shaft and the inner thread of the protruding end are threaded such that clockwise rotation of the knob retracts the shaft into the inner thread of the protruding end. The net result is that as the knob is turned clockwise, the shaft is pulled into the opening of the sleeve quickly because the knob is extending away from the sleeve and the shaft is being drawn into the protruding end of the knob at the same time.

Additionally, a surgeon can select any number of shafts with different sized jaws adapted to grasp a variety of grafts with different sizes and shapes.

The above objects may also be accomplished by a method that provides a sleeve with an opening; a shaft releasably movable within the opening of the sleeve; a bias jaw formed on one end of the shaft, the bias jaw adapted to grasp a surgical implant having a predetermined size; and an actuator releasably coupled to the other end of the shaft, wherein a first directional rotation of the actuator causes the bias jaw to retract relative to the opening of the sleeve to close the bias jaw, and counter-rotation to the first directional rotation of the actuator causes the bias jaw to protract relative to the opening of the sleeve to open the bias jaw.

Furthermore, the above objects may be accomplished by a method comprising the steps of: providing a sleeve with an opening; selecting a shaft with a jaw on one end adapted to grasp a particular sized surgical implant; inserting the shaft into the opening of the sleeve; coupling an actuator to the other end of the shaft, wherein a first directional rotation of the actuator causes the jaw to retract relative to the opening of the sleeve to close the jaw, and counter-rotation to the first directional rotation of the actuator causes the jaw to protract relative to the opening of the sleeve to open the jaw; positioning the surgical implant within the jaw, and rotating the actuator in the first directional rotation to grasp the surgical implant.

The above-described and many other features and attendant advantages of the present invention will become apparent from a consideration of the following detailed description when considered in conjunction with the accompanying drawings.

BRIEF DESCRIPTION OF THE DRAWINGS

Detailed description of the preferred embodiment of the invention will be made with reference to the accompanying drawings.

FIG. 9 is a cross-sectional view of one embodiment of the present invention according to FIG. 1, with the jaw in the retracted position relative to the shaft.

DETAILED DESCRIPTION OF THE INVENTION

This description is not to be taken in a limiting sense, but is made merely for the purpose of illustrating the general principles of the invention. The section titles and overall organization of the present detailed description are for the purpose of convenience only and are not intended to limit the present invention.

The present invention is directed to an apparatus and method of quickly and easily grasping and releasing a bone graft or other implant. The apparatus includes a sleeve with an opening through the axis of the sleeve. Within the opening of the sleeve is a shaft with a jaw on one end, and a threaded end on the opposite end. The sleeve has a square-section end that is adjacent to the jaw of the shaft. Furthermore, the shaft near the jaw has a square cross-section so that the shaft is substantially prevented from rotating but allowed to move axially along the opening of the sleeve. A knob is also rotatably coupled to the opening of the sleeve on the opposite end of the tip end. The knob has a protruding end which has an outer thread on the surface of the protruding end and an internal thread inside an axial center bore. The outer thread of the protruding end is adapted to rotatably couple to the opening on the sleeve, and the internal thread of the protruding end is adapted to rotatably couple to the threaded end of the shaft. The opening on the sleeve and the outer thread on the protruding end of the knob are threaded such that clockwise rotation of the knob extends the knob relative to the opening on the sleeve. Furthermore, the threaded end of the shaft and the center thread of the protruding end are threaded such that clockwise rotation of the knob retracts the shaft into the center thread of the protruding end. The net result is that as the knob is turned clockwise, the shaft is pulled into the opening of the sleeve quickly because the knob is extending away from the sleeve and the shaft is being inserted into the protruding end of the knob at the same time. As the shaft is being retracted into the tip end of the sleeve, the tip end bears on the jaw to close the jaw quickly and conversely opens quickly as the shaft protracts from the tip end.

Figure 1:
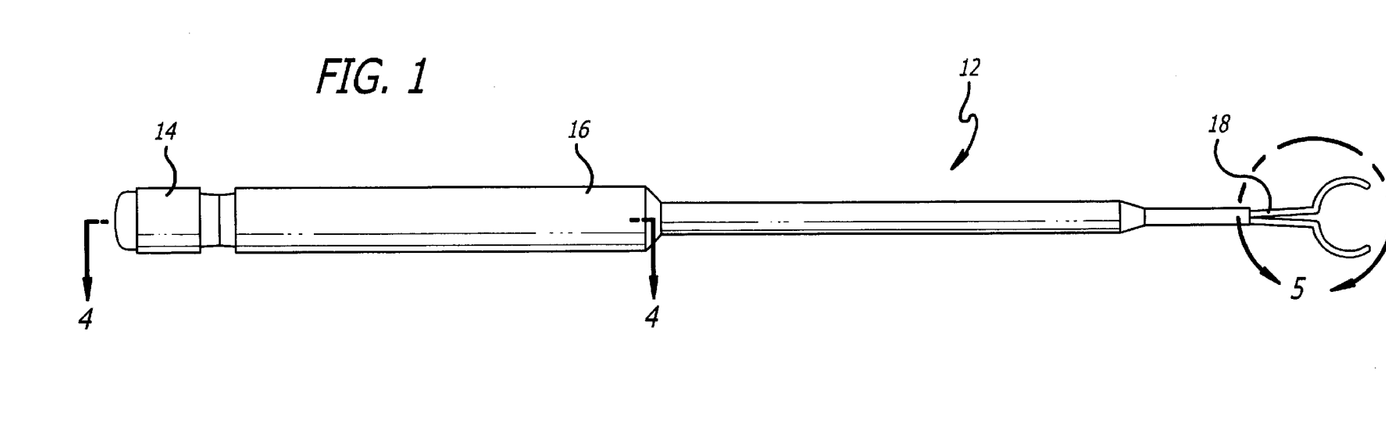
FIG. 1 is a side view of one embodiment of the present invention with a sleeve shaft and a knob in the assembled position.
Figure 2:
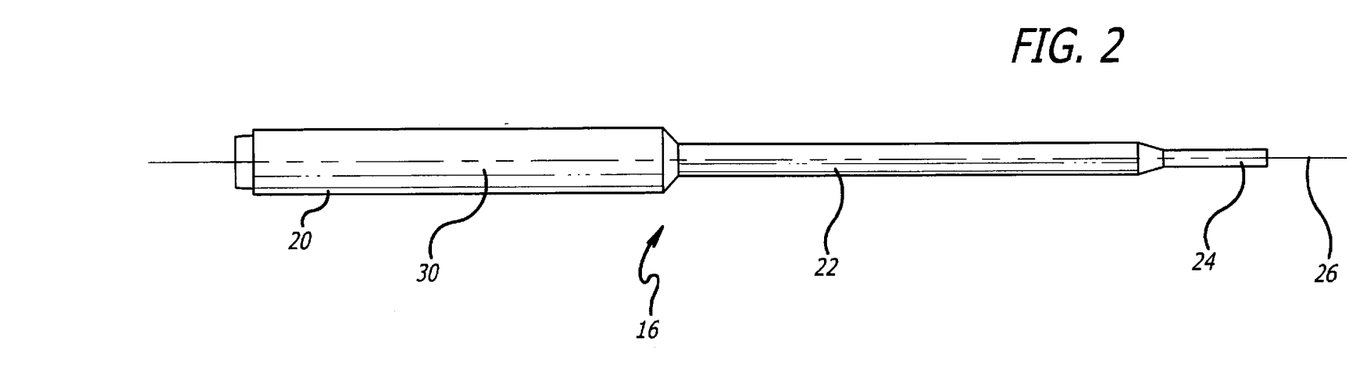
FIG. 2 is a side view of the exemplary embodiment of the present invention according to FIG. 1 without the shaft and the knob.
Figure 4:
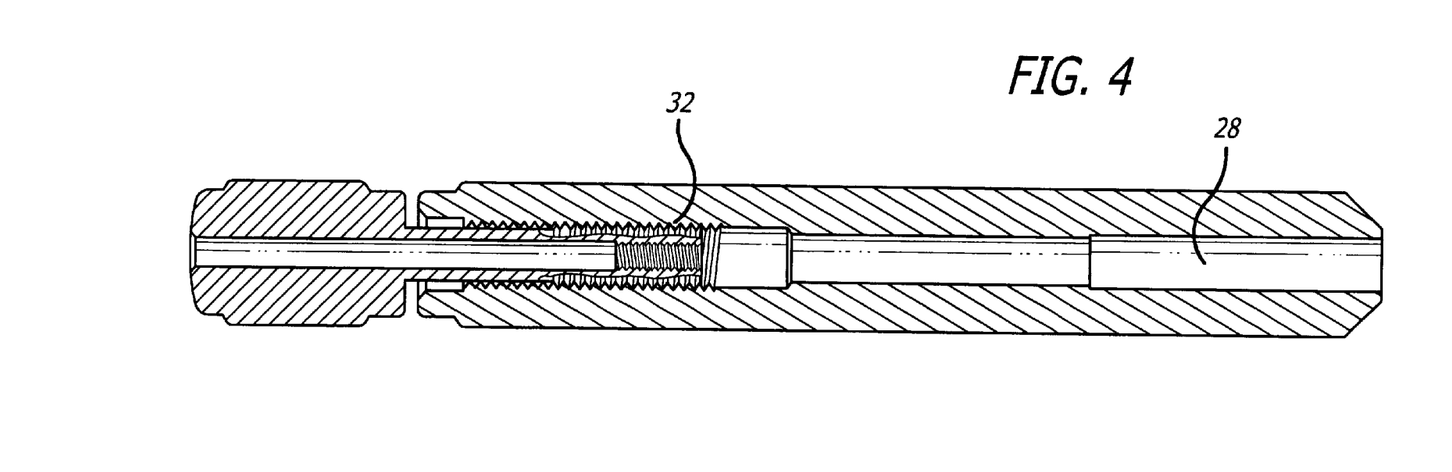
FIG. 4 is a cross-sectional view of an exemplary knob and sleeve along the line 4—4 in FIG. 2.

FIG. 1 illustrates, by way of example, one embodiment of an inserter device assembly 12 (hereinafter inserter) includes a knob 14 (or actuator), a sleeve 16, and a shaft 18. As best shown in FIG. 2, the sleeve 16 includes a handle region 20, a tubular region 22, and a tip region 24. Furthermore, the sleeve 16 has an opening 28 (see FIG. 4) along the center line axis 26 running through the handle region 20, the tubular region 22, and the tip region 24. The exemplary handle 20 has a circumference and configuration suitable for gripping with one hand. To further enhance the gripping of the handle 20, the outer surface of the handle 20 may be provided with knurlings 30 or other suitable ridges or grooves to aid in gripping the handle 20. As further illustrated by way of example in FIG. 4, the free end of the handle 20 that associates with the knob 14 has an inner thread 32 along the opening 28 of the handle 20.

Figure 7:
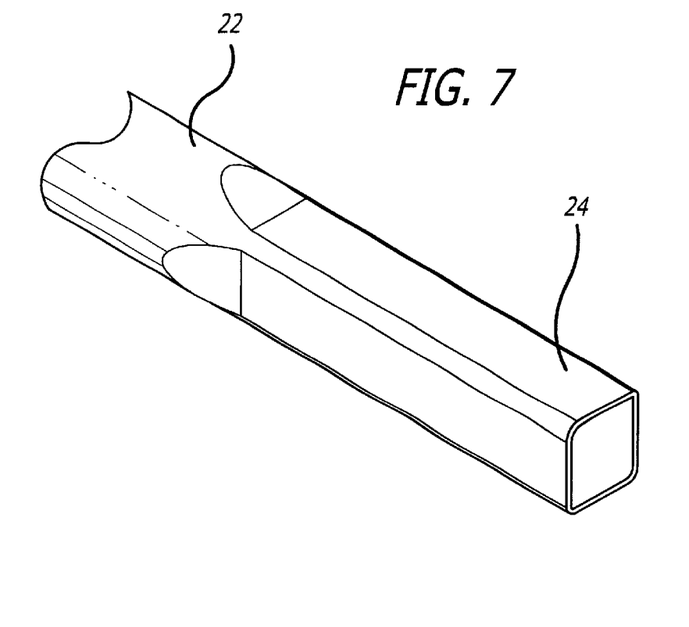
FIG. 7 is an enlarged perspective view of the tip region of the shaft.

As further illustrated by way of example in FIG. 2, the tubular region 22 may be fixedly or releasably coupled to the handle region 20. The tubular region 22 may have a variety of cross-sections such as square or circular cross-section as shown in FIG. 7. In this example, the tip region 24 may be formed to provide a square cross-section as shown by way of example in FIG. 7. However, the tip region 24 may be formed of other cross-sections, such as a rectangular cross-section.

Figure 3:
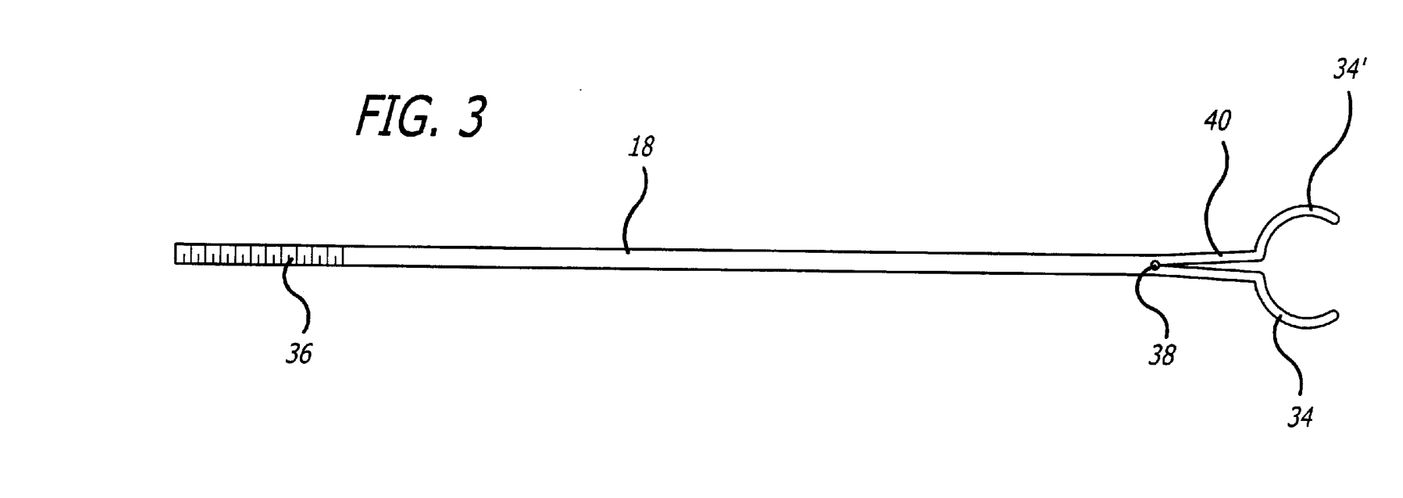
FIG. 3 is a side view of an exemplary shaft with a jaw on one end, and threaded end on the opposite end.
Figure 8:
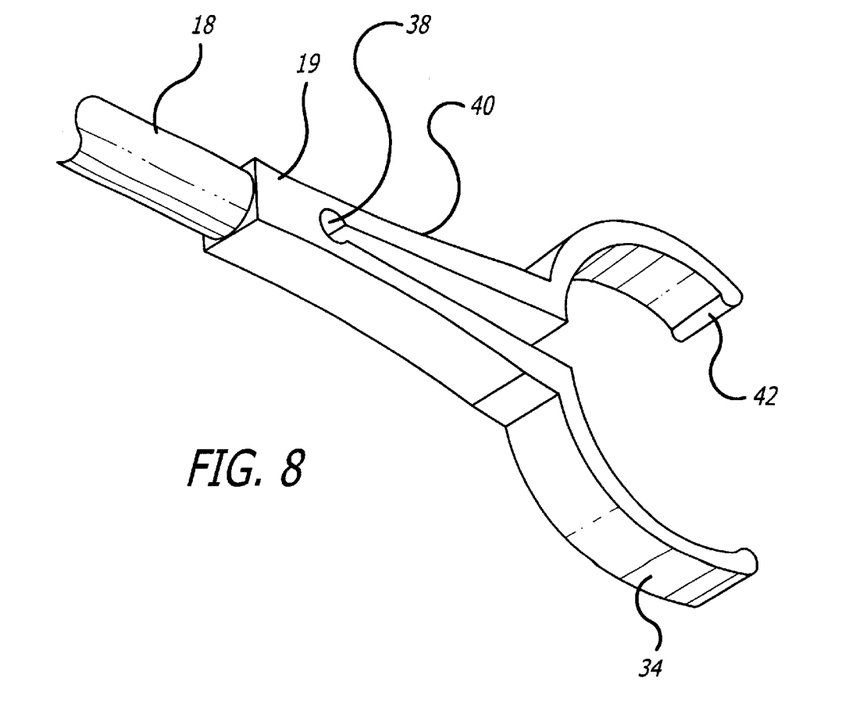
FIG. 8 is an enlarged perspective view of an exemplary jaw.

FIG. 3 illustrates by way of example the shaft 18 with a jaw or jaws 34 on one end and a threaded end 36 on the opposite end. The jaw 34 is formed by splitting the shaft 18 beginning at a hole 38. Splitting the shaft 18 forms a fork 40 which is shaped to form the jaw 34. As illustrated by way of example in FIG. 8, the shaft 18 transitions to form a square cross-section about a base 19 of the jaw, which is smaller than the square cross-section of the tip region 24 so that the base 19 may slide within the tip region 24. The flexibility of the fork is determined by the size of the hole 38; that is, increase in diameter of the hole 38 increases the flexibility of the fork 40. An exemplary diameter of the hole 38 may vary between approximately 0.50–5.0 mm. The shaft 18 may be formed of a variety of cross-sectional members such as circular and square. However, as illustrated in FIG. 8, the cross-section of the base of the jaw is substantially square or rectangular in shape, which is substantially similar to the square cross-section of the tip region 24. Alternatively, the jaw 34 may be formed separately and coupled to the shaft 18 about base 19.

Figure 5:
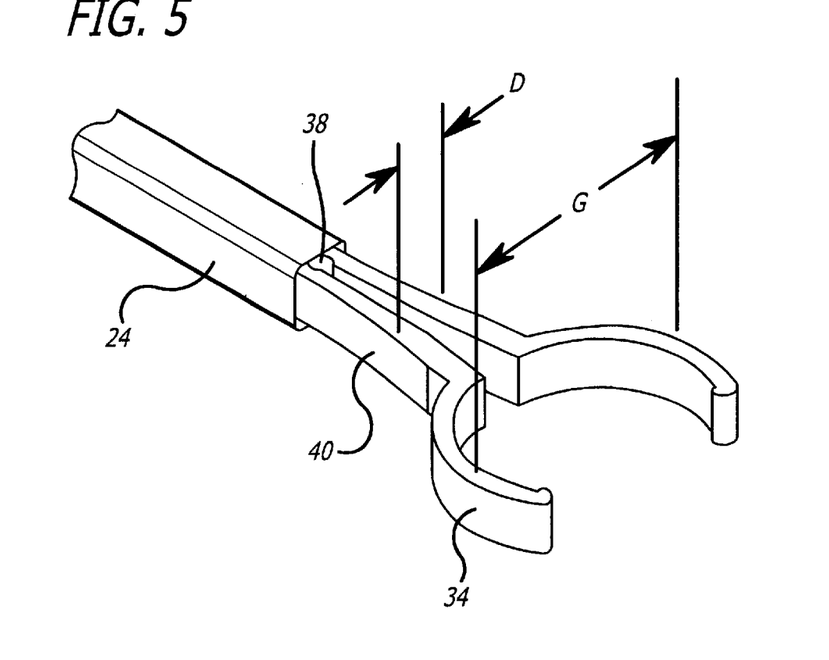
FIG. 5 is an enlarged perspective view of the encircled area 5 of FIG. 1.

As illustrated by way of example in FIG. 5, the distance "D" between the fork 40 gradually increases from the hole 38 to the jaw 34. For example, near the hole 38, the distance D is slightly less than the size of the square cross-section in the tip region 24. However, near the jaw 34, the distance D of the fork 40 is greater than the side of the square cross-section along the tip region 24, so that as the shaft 18 is drawn into the tip region 24, the side walls of the square tip region 24 bears on the fork 40 causing the fork to close (see FIG. 10), but as the shaft 18 is withdrawn from the tip region 24, the bias or the flexibility in the fork 40 expands to open the jaw 34 (see FIG. 9). Furthermore, the square cross-section of the base of the fork sliding within the square tip region 24 prevents the fork 40 from rotating relative to the tip region 24. In other words, there is very little rotation in the shaft 18, if at all, and generally only moves in the axial direction.

With regard to the jaw 34, the fork 40 is shaped to form an arc as shown by way of example in FIG. 8. In this example, the arc of the jaw 34 is greater than 180 degrees. That is, the circumference of the jaw 34 is greater than a half-circle. Furthermore, as illustrated in FIG. 8, along the tip of the jaw 34 is a lip 42 that forms a slight hook so that a graft held within the jaw is securely held. The lip 42 also ensures that the graft is securely held within the jaw 34 when it is being pulled.

As shown by way of example in FIG. 5, the shaft 18 may be made with a jaw 34 having a different gap "G". For example, a surgeon may have three different shafts 18, with a jaw 34 having three different gap sizes, such as 13 mm, 16 mm, and 18 mm, at rest, that is when there is no force being applied to the fork 40. In the fully closed position, the gap sizes would decrease to approximately 10 mm, 12 mm and 14 mm respectively. Of course, a shaft 18 with different gap sizes is within the scope of the present invention. Furthermore, configuration of the jaw 34 is not limited to the arc shaped jaw as shown in FIG. 3. That is, the configuration of the jaw 34 may be adapted to hold any irregularly shaped graft. Such configuration may include a jaw 34 that diverges off on an angle and converging back into the center line. Also, a lip 42 may also be formed within the jaw 34 to further assist in positioning the graft and holding it in its place. Alternatively, a surgeon may be provided with three inserters with a jaw having three different gap sizes.

Figure 6:
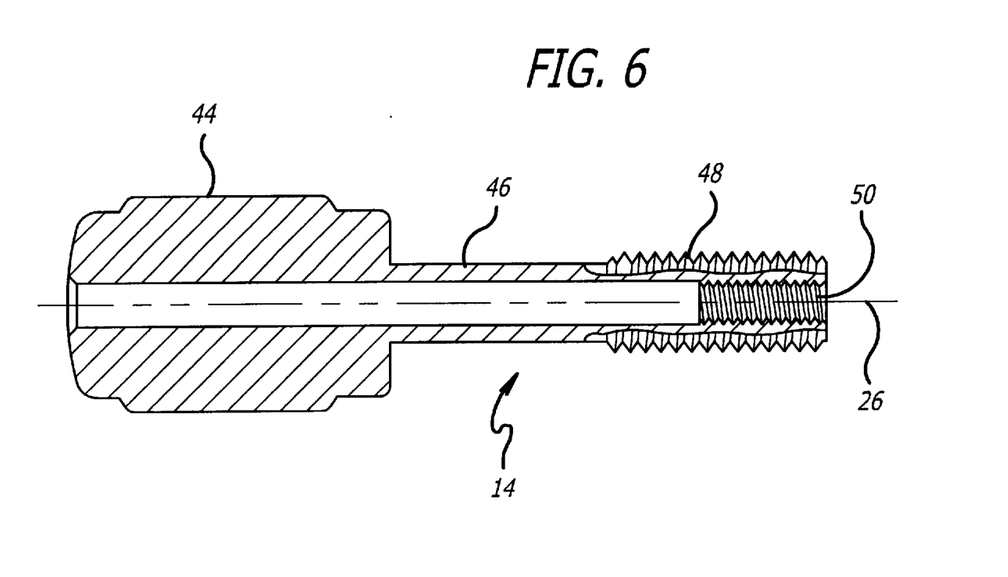
FIG. 6 is an enlarged cross-sectional view of the knob along the line 4—4 in FIG. 1.

As illustrated by way of example in FIG. 6, the knob 14 includes a grasping end 44 and a protruding end 46. On the surface of the protruding end 46 is an outer thread 48 machined to associate with the inner thread 32 on the sleeve 16. Additionally, along the center line 26 of the knob 14 is an internal thread 50 machined to associate with the threaded end 36 of the shaft 18. As the knob 14 is turned in a certain direction, such as a clockwise direction, the outer thread 48 and the inner thread 32 are threaded to cause the knob 14 to extend relative to the sleeve 16. At the same time, as the knob 14 is turned in a clockwise direction, the center thread 50 and the threaded end 36 are threaded to cause the threaded end 36 to retract into the internal thread 50. The net result is that the fork 40 is retracted into the tip region 24 at a faster rate because as the threaded end 36 is retracted into the internal thread 50, the knob 14 is also being extended relative to the sleeve 16. Thus, there is dual relative motion along the center axis 26 to retract the jaw 34 into the tip region 24. Conversely, as the knob is turned in the counter direction, i.e., counter-clockwise in this example, the jaw retracts from the tip region 24 at a faster rate. Although this example describes the clockwise direction as the certain direction which causes the jaw to retract into the tip region, it is within the scope of this invention to machine the threads to have the counter clockwise direction as the certain directional rotation which causes the jaw to retract into the tip region.

The dual relative motion causes the jaw to retract and protract relative to the tip region 24 at a faster rate so that a surgeon can grasp and release the graft faster to save valuable time during surgery. Also, the rate at which the shaft slides within the sleeve may also vary depending on the pitch of the thread.

Figure 9:
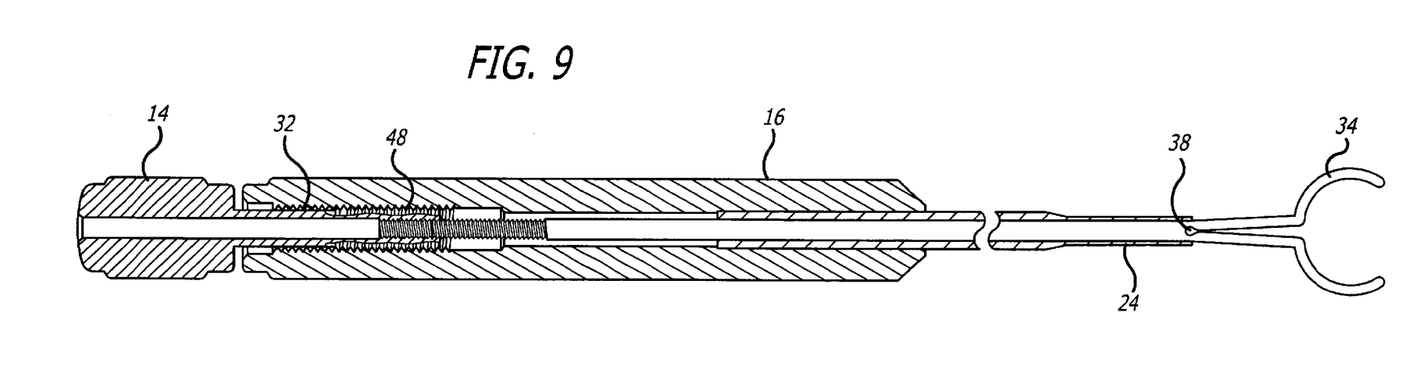
FIG. 9 is a cross-sectional view of one embodiment of the present invention according to FIG. 1, with the jaw in the extended position relative to the shaft; and FIG. 10
Figure 10:
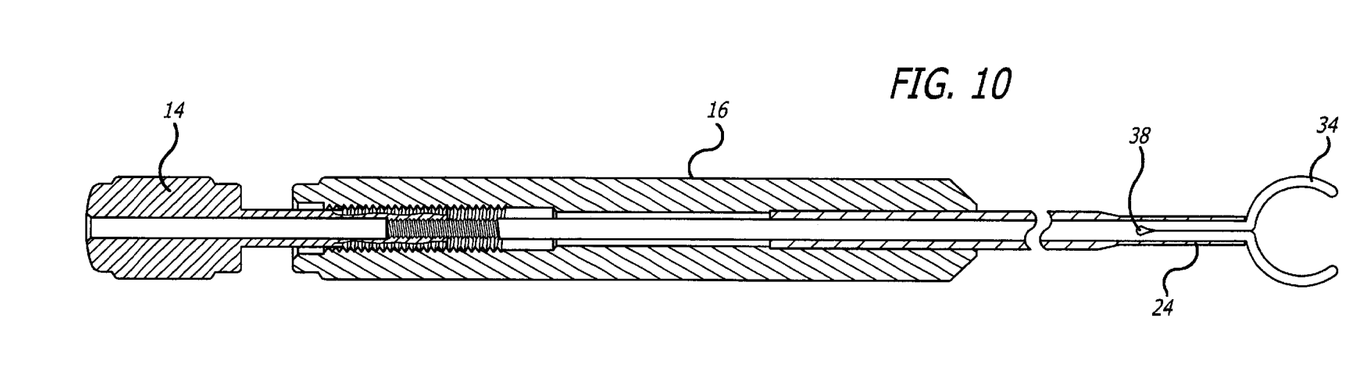

As an example, during surgery, a surgeon may select from a variety of shafts with a particular jaw best suited for that surgery; that is, the configuration and size of the jaw. Once a shaft is selected, the threaded end of the shaft is inserted into the opening 28 of the sleeve 16. Then the protruding end 46 of the knob 14 is rotated into the sleeve 16 via the outer thread 48 and inner thread 32, as shown in FIG. 9. In this example, the protruding end 46 is inserted into the sleeve 16 by counter-clockwise rotation of the knob 14. Once the protruding end 46 is fully inserted into the sleeve 16, the clockwise rotation of the knob will engage the threaded end 36 into the center thread 50, as shown in FIG. 10. Note that the square tip region 24 will prevent the fork and conversely the jaw from rotating so that the shaft can only move in the axial direction. Accordingly, once the knob is fully inserted into the sleeve by a counter-clockwise rotation, a surgeon positions the graft within the jaw, which may have been specially adapted to hold a graft. As illustrated in FIGS. 1 and 9, when the knob is fully inserted into the inner thread 32 and the shaft 18 is fully inserted into the opening 28, the hole 38 of the shaft is substantially near the tip region 24. On the other hand, as illustrated in FIG. 10, when the knob is in the fully protracted position the jaw 34 is substantially near the tip region 24.

To firmly hold the graft, the surgeon then turns the knob in the clockwise direction which retracts the jaw into the tip region which causes the tip region to apply compressive force on the fork, thereby causing the gap of the jaw to close to apply pressure on the graft. Note that the pressure applied to the graft is transferred through the shaft to the knob 14 so that as the surgeon is turning the knob, the surgeon can sense the pressure applied to the graft due to the resistance in the knob from turning. To ensure that the jaw does not apply excessive force on the graft, the diameter of the hole 38 may be increased, which adds additional flexibility to the jaw 34. With the graft securely held within the jaw, the surgeon, with the assistance of the inserter assembly, positions the graft between the vertebral bodies, then turns the knob in the counter-clockwise direction to release the graft from the jaw quickly.

Another advantage of the present invention is that the circumference of the square tip region 24 is relatively small so that it does not obstruct the surgeon's view. Also, a smaller tip region means that the surgeon can make a smaller cut within the surgical area to insert the graft.

Once the surgeon is done with the surgery, the inserter assembly may be easily cleaned or sterilized by disassembling the inserter device into a separate knob, sleeve, and shaft. Thus, the inserter assembly disengages into three separate pieces and can be easily cleaned.

With regard to material, the inserter assembly should be made of material that is lightweight, strong, flexible and resistive to corrosion. For example, the knob and the sleeve may be made of plastic, aluminum, stainless steel, and/or titanium. With regard to the shaft, it may be made of titanium alloy, such as Ti 6-Al/4V for its strength and flexibility and resistance to corrosion or from an appropriate stainless steel alloy such as 17-4 Ph, 15-5 Ph, 410 or 420. Alternatively, any other material know to one of ordinary skilled in the art is within the scope of the present invention. Additionally, the configuration and size of the jaw may be adapted to hold a variety of grafts, such as allograft (human bone from a donor), homolograft (patient's own bone), and xenegraft (bone from another species), which may be irregularly shaped and of a variety of sizes.

Although the present invention has been described in terms of the exemplary embodiment above, numerous modifications and/or additions to the above-described embodiments would be readily apparent to one skilled in the art. Accordingly, the present invention is not limited to the precise embodiments described in detail hereinabove. For example, the knob and the shaft may be fixedly coupled and the free end of the shaft may be threaded to rotatably couple to the base of the jaw, which is also threaded to receive the threaded end of the shaft. With respect to the claims, it is applicant's intention that the claims not be interpreted in accordance with the sixth paragraph of 35 U.S.C. § 112 unless the term "means" is used following by a functional statement.

What is claimed is:

1. An inserter assembly comprising:
 a sleeve having an opening there through between a first end and a second end;

a knob, the knob and the first end of the sleeve adapted to rotatably couple to each other, wherein a first directional rotation of the knob causes the knob to move axially away from the first end of the sleeve, and the counter-rotation of the first directional rotation of the knob causes the knob to move axially toward the first end of the sleeve;

the knob having a bore;

a shaft adapted to move axially within the opening of the sleeve, the shaft having a clamp end and an opposite end, the opposite end of the shaft and the bore of the knob adapted to rotatably couple to each other, wherein the first directional rotation of the knob causes the clamp end of the shaft to move axially toward the second end of the sleeve, and the counter-rotation of the first directional rotation of the knob causes the clamp end of the shaft to move axially away from the second end of the sleeve; and the clamp having a pair of bias fingers which close as the clamp moves axially toward the opening of the second end of the sleeve.

2. An inserter assembly according to claim 1 wherein the knob has a protruding end adapted to rotatably couple to the opening on the first end of the sleeve.

3. An inserter assembly according to claim 1 wherein between the first and second ends of the sleeve is a transitional region, wherein between the first end and the transitional region defines a handle, and between the transitional region and the second end of the sleeve defines a tapered tube, wherein the tapered tube has a smaller circumference than the handle.

4. An inserter assembly according to claim 3 wherein the second end of the tapered tube has a square opening.

5. An inserter assembly according to claim 1 wherein the second end of the tapered tube has a rectangular opening.

6. An inserter assembly according to claim 3 wherein the handle has a grooved surface for gripping.

7. An inserter assembly according to claim 2 wherein the shaft divides into a fork on the clamp end to form the pair of bias fingers, wherein the fork has a square cross-section adapted to move axially within the square cross-sectional opening on the second end of the sleeve, wherein the square cross-sectional opening prevents the fork from rotating as the knob is rotated.

8. An inserter assembly according to claim 7 wherein the shaft has a predetermined size hole where the shaft divides into the fork, wherein the predetermined size hole determines the flexibility of the bias fingers.

9. An inserter assembly according to claim 7, wherein the opening on the second end of the sleeve causes the pair of bias fingers to close as the fork moves axially toward the second end of the handle, and the pair of bias fingers open as the fork moves axially away from the second end of the handle.

10. An inserter assembly according to claim 9 wherein the arc of the fingers is greater than approximately 180 degrees.

11. An inserter assembly according to claim 1 wherein the bias fingers form an arc with a tip on each of the fingers.

12. An inserter assembly according to claim 11 wherein each of the tips on the bias fingers has a lip.

13. An inserter assembly according to claim 1 wherein the knob and the first end of the sleeve are threaded to rotatably couple to each other.

14. An inserter assembly according to claim 1 wherein the knob has an internal thread adapted to associate with the opposite end of the shaft that has a thread adapted to rotatably couple to said knob.

15. An inserter assembly, comprising:

a sleeve with an opening;

a shaft releasably movable within the opening of the sleeve;

a bias jaw formed on one end of the shaft; and an actuator releasably coupled to the other end of the shaft, wherein a first directional rotation of the actuator causes the bias jaw to retract relative to the opening of the sleeve to close the bias jaw, and counter-rotation to the first directional rotation of the actuator causes the bias jaw to protract relative to the opening of the sleeve to open the bias jaw, the actuator releasably coupled to the sleeve, wherein the first directional rotation of the actuator causes the actuator to extend relative to the opening of the sleeve to cause the bias jaw to retract relative to the opening of the sleeve faster, and wherein the counter-rotation of the first directional rotation of the actuator causes the bias jaw to protract relative to the opening of the sleeve faster.

16. An inserter assembly according to claim 15 wherein the sleeve adjacent the bias jaw has a tapered end.

17. An inserter assembly according to claim 16 wherein the tapered end of the sleeve has a square or rectangular cross-sectional opening.

18. An inserter assembly according to claim 17 wherein the shaft splits into a fork to form the bias jaw, wherein the fork has a square cross-section adapted to move axially within the square cross-sectional opening on the tapered end of the sleeve, wherein the square cross-sectional opening prevents the square cross-sectional fork from rotating as the actuator is rotated.

19. An inserter assembly according to claim 15 wherein the actuator is threaded and the opening of the sleeve is threaded to rotatably couple to the actuator.

20. An inserter assembly according to claim 15 wherein the other end of the shaft and the actuator are threaded to rotatably couple to each other.

21. An inserter assembly according to claim 15 wherein the shaft is replaceable with a second shaft with a different bias jaw adapted to grasp a different size surgical implant.

22. A method of quickly grasping and releasing a variety of sizes of surgical implants, comprising the steps of:

providing a sleeve with an opening;

inserting a shaft into the opening of the sleeve;

providing a jaw on one end of the shaft;

coupling an actuator to the other end of the shaft, wherein a first directional rotation of the actuator causes the jaw to retract relative to the opening of the sleeve to close the jaw, and counter-rotation to the first directional rotation of the actuator causes the jaw to protract relative to the opening of the sleeve to open the jaw;

coupling the actuator to the sleeve, wherein a the first directional rotation of the actuator causes the actuator to move axially away from the sleeve, and counter-rotation of the first directional rotation of the actuator causes the actuator to move axially toward the sleeve, positioning the surgical implant within the jaw; and rotating the actuator in the first directional rotation to grasp the surgical implant.

23. A method according to claim 22 wherein the sleeve adjacent the jaw has a square cross-sectional opening end, and the shaft adjacent the jaw has a square cross-sectional end, wherein the square cross-sectional opening end of the sleeve prevents the square cross-sectional shaft end from rotating as the actuator is rotated.

24. A method according to claim 22 wherein the actuator is releasably coupled to the sleeve, wherein the first directional rotation of the actuator causes the actuator to extend relative to the opening of the sleeve to cause the jaw to quickly retract relative to the opening of the sleeve, and the counter-rotation of the first directional rotation of the actuator causes the jaw to quickly protract relative to the opening of the sleeve.

* * * * *